(12) United States Patent
Albaneze-Walker

(10) Patent No.: US 11,530,179 B2
(45) Date of Patent: Dec. 20, 2022

(54) AMORPHOUS SOLID SUCCINYLATED 3-(FATTY ACID AMIDO)-2-HYDROXY-1-(PROTECTED HYDROXY)-PROPANE SALTS AND METHODS OF MAKING THE SAME

(71) Applicant: Geron Corporation, Foster City, CA (US)

(72) Inventor: Jennifer E. Albaneze-Walker, Foster City, CA (US)

(73) Assignee: Geron Corporation, Foster City, CA (US)

(*) Notice: Subject to any disclaimer, the term of this patent is extended or adjusted under 35 U.S.C. 154(b) by 237 days.

(21) Appl. No.: 17/079,129

(22) Filed: Oct. 23, 2020

(65) Prior Publication Data

US 2021/0147344 A1 May 20, 2021

Related U.S. Application Data

(60) Provisional application No. 62/926,778, filed on Oct. 28, 2019.

(51) Int. Cl.
*C07C 235/00* (2006.01)
*C07C 231/12* (2006.01)

(52) U.S. Cl.
CPC .......... *C07C 235/00* (2013.01); *C07C 231/12* (2013.01)

(58) Field of Classification Search
None
See application file for complete search history.

(56) References Cited

U.S. PATENT DOCUMENTS

| | | |
|---|---|---|
| 9,266,816 B2 | 2/2016 | Shrawat et al. |
| 9,657,296 B2 | 5/2017 | Gryaznov et al. |
| 2006/0069156 A1 | 3/2006 | Darteil et al. |
| 2006/0121583 A1 | 6/2006 | Lassalle et al. |
| 2006/0154984 A1 | 7/2006 | Darteil et al. |
| 2009/0048427 A1 | 2/2009 | Hedgpeth et al. |
| 2011/0286937 A1 | 11/2011 | Kiso et al. |
| 2017/0130225 A1 | 5/2017 | Gryaznov et al. |

FOREIGN PATENT DOCUMENTS

| | | |
|---|---|---|
| WO | WO1996032496 A2 | 10/1996 |
| WO | WO2019011829 A1 | 1/2019 |

OTHER PUBLICATIONS

PUBCHEM-CID: 11002017 Create Date: Oct. 26, 2006 (Oct. 26, 2006) pp. 1-11; p. 2.

*Primary Examiner* — Clinton A Brooks
*Assistant Examiner* — Jennifer C Sawyer
(74) *Attorney, Agent, or Firm* — Rudy J. Ng; Khin K. Chin; Bozicevic, Field & Francis LLP

(57) ABSTRACT

Aspects of the disclosure includes methods for preparing an amorphous solid composition of a fatty acid metal salt. In practicing the subject methods according to certain embodiments, a succinylated 3-(fatty acid amido)-2-hydroxy-1-(protected hydroxy)-propane organic salt is contacted with a metal base to produce a succinylated 3-(fatty acid amido)-2-hydroxy-1-(protected hydroxy)-propane metal salt; and the succinylated 3-(fatty acid amido)-2-hydroxy-1-(protected hydroxy)-propane metal salt is precipitated in a solvent to produce an amorphous solid succinylated 3-(fatty acid amido)-2-hydroxy-1-(protected hydroxy)-propane metal salt composition. An amorphous solid succinylated 3-(fatty acid amido)-2-hydroxy-1-(protected hydroxy)-propane lithium salt is also provided.

21 Claims, 4 Drawing Sheets

AMORPHOUS SOLID SUCCINYLATED 3-(FATTY ACID AMIDO)-2-HYDROXY-1-(PROTECTED HYDROXY)-PROPANE SALTS AND METHODS OF MAKING THE SAME

CROSS-REFERENCE TO RELATED APPLICATIONS

This application claims benefit of priority to U.S. Provisional Patent Application Ser. No. 62/926,778 filed Oct. 28, 2019, the disclosure of which is herein incorporated by reference.

INTRODUCTION

Imetelstat is a telomerase inhibitor that binds with high affinity to the template region of the RNA component of telomerase. Studies have shown that imetelstat inhibits telomerase activity and is effective against cell proliferation in a multitude of different cancer cell lines and human tumors. Imetelstat has been used in clinical trials of patients with hematologic malignancies. A clinical trial of patients with myelofibrosis showed that imetelstat was able to achieve complete clinical remissions in certain patients.

The structure of imetelstat includes a N3'→P5' thiophosphoramidate oligonucleotide. The synthesis of imetelstat has been carried out by solid phase oligonucleotide synthesis where the first phosphoramidite nucleotide is coupled to the support followed by sulfurization. Chain elongation of the oligonucleotide component is achieved by repeated reaction of the 3'-amino group of the solid-phase support bonded oligonucleotide with additional nucleotide phosphoramidite monomers. The oligonucleotide of imetelstat is coupled to the solid phase support through a palmitoyl-amide linker. This fatty acid-amide linker is thus a component in the synthesis of imetelstat.

SUMMARY

Aspects of the disclosure includes methods for preparing an amorphous solid composition of a fatty acid metal salt. In embodiments, the subject methods include preparing a fatty acid metal salt from a fatty acid organic salt and precipitating the fatty acid metal salt from a solvent to produce an amorphous solid composition of the fatty acid metal salt. In practicing the subject methods according to certain embodiments, a succinylated 3-(fatty acid amido)-2-hydroxy-1-(protected hydroxy)-propane organic salt is contacted with a metal base to produce a succinylated 3-(fatty acid amido)-2-hydroxy-1-(protected hydroxy)-propane metal salt; and the succinylated 3-(fatty acid amido)-2-hydroxy-1-(protected hydroxy)-propane metal salt is precipitated in a solvent to produce an amorphous solid succinylated 3-(fatty acid amido)-2-hydroxy-1-(protected hydroxy)-propane metal salt composition. (Scheme I)

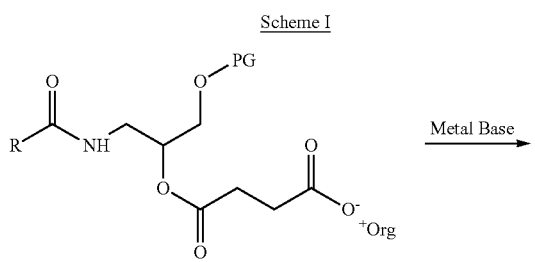

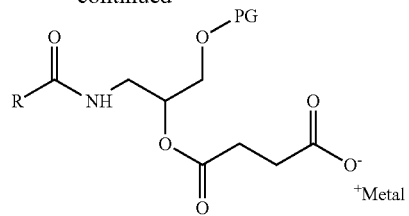

where R is a $C_{10}$-$C_{20}$ fatty acid (e.g. a $C_{16}$ fatty acid); and PG is a protecting group.

In some embodiments, the metal is lithium. In some embodiments, the fatty acid is selected from palmitic acid, stearic acid, oleic acid, linoleic acid, myristoleic acid and batyl fatty acid. In some embodiments, the protected hydroxy group includes a dimethoxy-triphenylmethyl protecting group. In certain embodiments, the succinylated 3-(fatty acid amido)-2-hydroxy-1-(protected hydroxy)-propane metal salt is a compound of Formula I:

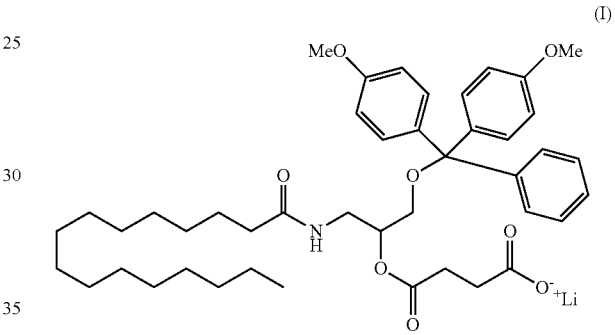

The amorphous composition may be formed as a crude composition. In certain instances, the fatty acid metal salt has a purity of 95% or more by weight of the crude composition (e.g., as determined by high performance liquid chromatography (HPLC), proton nuclear magnetic resonance spectroscopy ($^1$H NMR) or a combination thereof).

In some embodiments, precipitating the succinylated 3-(fatty acid amido)-2-hydroxy-1-(protected hydroxy)-propane metal salt to produce the amorphous solid composition includes: 1) heating the succinylated 3-(fatty acid amido)-2-hydroxy-1-(protected hydroxy)-propane metal salt in a non-polar solvent to produce a heated succinylated 3-(fatty acid amido)-2-hydroxy-1-(protected hydroxy)-propane metal salt composition; and 2) cooling the heated succinylated 3-(fatty acid amido)-2-hydroxy-1-(protected hydroxy)-propane metal salt composition to form an amorphous solid of the succinylated 3-(fatty acid amido)-2-hydroxy-1-(protected hydroxy)-propane metal salt. In certain instances, the succinylated 3-(fatty acid amido)-2-hydroxy-1-(protected hydroxy)-propane metal salt is heated in the non-polar solvent to a temperature of from about 45° C. to about 55° C., such as about 50° C. To precipitate the amorphous solid composition, the heated succinylated 3-(fatty acid amido)-2-hydroxy-1-(protected hydroxy)-propane metal salt composition may be cooled to a temperature of from about −5° C. to about 5° C., such as about 0° C. to produce the amorphous solid composition. In certain instances, cooling the heated succinylated 3-(fatty acid amido)-2-hydroxy-1-(protected hydroxy)-propane metal salt composition includes inverse addition of the heated succinylated 3-(fatty acid amido)-2-hydroxy-1-(protected hydroxy)-propane metal salt composition to a cold non-polar solvent. The precipitated amorphous solid succinylated 3-(fatty acid amido)-2-hydroxy-1-(protected hydroxy)-propane metal salt composition may be isolated by filtration.

In certain embodiments, methods further include preparing the succinylated 3-(fatty acid amido)-2-hydroxy-1-(protected hydroxy)-propane organic salt by contacting a 3-(fatty acid amido)-2-hydroxy-1-(protected hydroxy)-propane with succinic anhydride in the presence of an organic base to succinylate the 2-hydroxy group of the 3-(fatty acid amido)-2-hydroxy-1-(protected hydroxy)propane. In some instances, the 3-(fatty acid amido)-2-hydroxy-1-(protected hydroxy)-propane is contacted with succinic anhydride in a polar solvent.

Aspects of the disclosure also include an amorphous solid succinylated 3-(fatty acid amido)-2-hydroxy-1-(protected hydroxy)-propane lithium salt. In some embodiments, the fatty acid is selected from palmitic acid, stearic acid, oleic acid, linoleic acid, myristoleic acid and batyl fatty acid. In some embodiments, the protected hydroxy group includes a dimethoxy-triphenylmethyl protecting group. In certain embodiments, the succinylated 3-(fatty acid amido)-2-hydroxy-1-(protected hydroxy)-propane metal salt is a compound of Formula I:

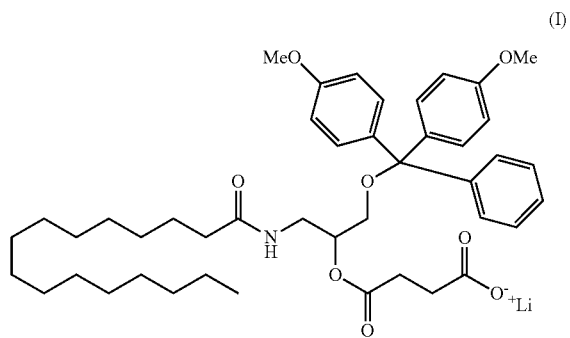 [SMILES: CCCCCCCCCCCCCCCC(=O)NCC(COC(c1ccccc1)(c1ccc(OC)cc1)c1ccc(OC)cc1)OC(=O)CCC(=O)[O-] ; [Li+]]
(I)

In some embodiments, the present disclosure provides an amorphous solid succinylated 3-(fatty acid amido)-2-hydroxy-1-(protected hydroxy)-propane lithium salt of Formula I having a peak at about 19.5° 2θ in an X-ray powder diffraction pattern (XRPD) with Cu Kα radiation. In other embodiments, the present disclosure provides an amorphous solid succinylated 3-(fatty acid amido)-2-hydroxy-1-(protected hydroxy)-propane lithium salt of Formula I where thermogravimetric analysis (TGA) exhibits a single weight loss step. In these embodiments, the single weight loss step may begin at about 225° C. The subject amorphous solid succinylated 3-(fatty acid amido)-2-hydroxy-1-(protected hydroxy)-propane lithium salt of Formula I may also be characterized by TGA thermogram that shows a mass loss of less than 1% of the total mass of the sample upon heating from 30° C. to 300° C. In other embodiments, the present disclosure provides an amorphous solid succinylated 3-(fatty acid amido)-2-hydroxy-1-(protected hydroxy)-propane lithium salt of Formula I, where the differential scanning calorimetry (DSC) curve exhibits an absorption peak at about 44.9° C.

SELECT DEFINITIONS OF CHEMICAL TERMINOLOGY

Figure 1:
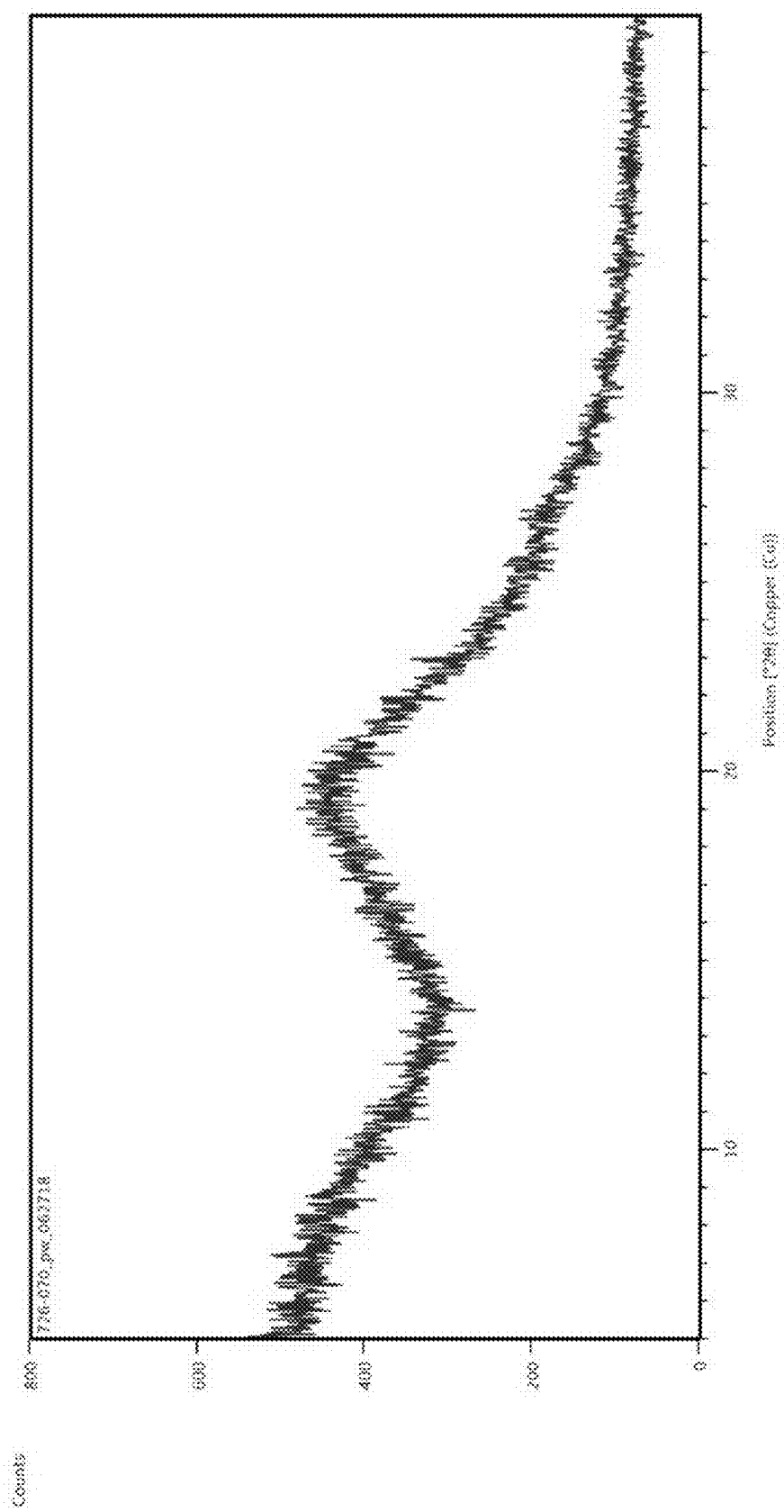
FIG. 1 shows an X-ray powder diffraction pattern of an amorphous solid succinylated 3-(palmitoyl amido)-2-hydroxy-1-(dimethoxytriphenylmethyl hydroxy)-propane lithium salt according to certain embodiments.

The following terms have the following meanings unless otherwise indicated. Any undefined terms have their art recognized meanings.

As used herein, the terms "phosphate" and "phosphate group" are meant to encompass a thiophosphate group and an oxophosphate group.

As used herein, the term "phosphoramidite amino group" refers to the amino group, —NR$^4$R$^5$, attached to the phosphorus atom of a phosphoramidite group, and the term "phosphoramidite nitrogen" refers to the nitrogen atom of the phosphoramidite amino group.

"Alkyl" refers to monovalent saturated aliphatic hydrocarbyl groups having from 1 to 10 carbon atoms and such as 1 to 6 carbon atoms (e.g., "an alkyl of 1 to 6 carbons atoms"), or 1 to 5 (e.g., "an alkyl of 1 to 5 carbons atoms"), or 1 to 4 (e.g., "an alkyl of 1 to 4 carbons atoms"), or 1 to 3 carbon atoms (e.g., "an alkyl of 1 to 3 carbons atoms"). This term includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. In some instances, a"substituted alkyl" refers to an alkyl group as defined herein having from 1 to 5 substituents selected from the group consisting of alkoxy, cycloalkyl, cycloalkenyl, acyl, acylamino, acyloxy, amino, aminoacyl, aminoacyloxy, oxyaminoacyl, azido, cyano, halogen, hydroxyl, carboxyl, carboxylalkyl, thiol, thioalkoxy, aryl, aryloxy, heteroaryl, heteroaryloxy, heterocyclyl, heterocyclooxy, sulfonamido, and —NR$^a$R$^b$, wherein R$^a$ and R$^b$ may be the same or different and are chosen from hydrogen, alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, N R$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O)NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. In such cases, an aryl group that is substituted with from 1 to 5 substituents (e.g., as described herein) is referred to as a "substituted aryl".

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O— alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O— substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl. In such cases, a heteroaryl group that is substituted with from 1 to 5 substituents (e.g., as described herein) is referred to as a "substituted heteroaryl".

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group $SO_2$-alkyl, $SO_2$-substituted alkyl, $SO_2$-alkenyl, $SO_2$-substituted alkenyl, $SO_2$-cycloalkyl, $SO_2$-substituted cycloalkyl, $SO_2$-cycloalkenyl, $SO_2$-substituted cycloalkenyl, $SO_2$-aryl, $SO_2$-substituted aryl, $SO_2$-heteroaryl, $SO_2$-substituted heteroaryl, $SO_2$-heterocyclic, and $SO_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-$SO_2$—, phenyl-$SO_2$—, and 4-methylphenyl-$SO_2$—.

"Sulfonyloxy" refers to the group —$OSO_2$-alkyl, $OSO_2$-substituted alkyl, $OSO_2$-alkenyl, $OSO_2$-substituted alkenyl, $OSO_2$-cycloalkyl, $OSO_2$-substituted cycloalkyl, $OSO_2$-cycloalkenyl, $OSO_2$-substituted cycloalkenyl, $OSO_2$-aryl, $OSO_2$-substituted aryl, $OSO_2$-heteroaryl, $OSO_2$-substituted heteroaryl, $OSO_2$-heterocyclic, and $OSO_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =$NR^{70}$, =N—$OR^{70}$, =$N_2$ or =S) on saturated carbon atoms in the specified group or radical are, unless otherwise specified, —$R^{60}$, halo, =O, —$OR^{70}$, —$SR^{70}$, —$NR^{80}R^{80}$, trihalomethyl, —CN, —OCN, —SCN, —NO, —$NO_2$, =$N_2$, —$N_3$, —$SO_2R^{70}$, —$SO_2O^-M^+$, —$SO_2OR^{70}$, —$OSO_2R^{70}$, —$OSO_2O^-M^+$, —$OSO_2OR^{70}$, —$P(O)(O^-)_2(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —OC(O)$R^{70}$, —OC(S)$R^{70}$, —OC(O) $O^-M^+$, —OC(O)$OR^{70}$, —OC(S)$OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a counter ion such as chloride, or two ionized compounds disclosed herein can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or -$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

"Stereoisomer" and "stereoisomers" refer to compounds that have same atomic connectivity but different atomic arrangement in space. Stereoisomers include cis-trans isomers, E and Z isomers, enantiomers, and diastereomers.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound. It is understood that the term "or a salt thereof" is intended to include all permutations of salts. It is understood that the term "or a pharmaceutically acceptable salt thereof" is intended to include all permutations of salts. It is understood that the term "or a solvate thereof" is intended to include all permutations of solvates. It is understood that the term "or a stereoisomer thereof" is intended to include all permutations of stereoisomers. It is understood that the term "or a tautomer thereof" is intended to include all permutations of tautomers. Thus for example it follows that it is intended to include a solvate of a pharmaceutically acceptable salt of a tautomer of a stereoisomer of subject compound.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, methods and materials of interest are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. When possible, this nomenclature has generally been derived using the commercially-available AutoNom software (MDL, San Leandro, Calif.).

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley- Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the compounds of the present disclosure, it may be necessary and/or desirable to protect sensitive or reactive groups on any of the molecules concerned. This can be achieved by means of conventional protecting groups as described in standard works, such as T. W. Greene and P. G. M. Wuts, "Protective Groups in Organic Synthesis", Fourth edition, Wiley, New York 2006. The protecting groups can be removed at a convenient subsequent stage using methods known from the art.

The compounds described herein can contain one or more chiral centers and/or double bonds and therefore, can exist as stereoisomers, such as double-bond isomers (i.e., geometric isomers), enantiomers or diastereomers. Accordingly, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

DETAILED DESCRIPTION

As summarized above, the present disclosure provides methods for preparing an amorphous solid composition of a fatty acid metal salt. In practicing the subject methods according to certain embodiments, a succinylated 3-(fatty acid amido)-2-hydroxy-1-(protected hydroxy)-propane organic salt is contacted with a metal base to produce a succinylated 3-(fatty acid amido)-2-hydroxy-1-(protected hydroxy)-propane metal salt; and the succinylated 3-(fatty acid amido)-2-hydroxy-1-(protected hydroxy)-propane metal salt is precipitated in a solvent to produce an amorphous solid composition of the fatty acid metal salt. The term "succinylated" is used herein in its conventional sense to refer to addition of a succinyl group ($—CO—CH_2—CH_2—CO_2H$) to the 3-(fatty acid amido)-2-hydroxy-1-(protected hydroxy)-propane (e.g., at the C-2 position of the 3-(fatty acid amido)-2-hydroxy-1-(protected hydroxy)-propane). In embodiments, the succinyl group can be added to the 3-(fatty acid amido)-2-hydroxy-1-(protected hydroxy)-propane by any convenient succinylation protocol, such as for example by reaction with succinic anhydride in the presence of a base (e.g., organic base, such as triethylamine). By "fatty acid amido" is meant a structural moiety that includes an aliphatic group bonded to an amide group ($—R—CO—N—R'—$, where R is an aliphatic chain of $C_{10}$-$C_{20}$, such as $C_{16}$ and R' is the C3 carbon of the 2-hydroxy-1-(protected hydroxy) propane). In embodiments (as described in greater detail below), the fatty acid may be an aliphatic chain $C_{10}$-$C_{20}$, such as $C_{16}$ alkyl chain. The fatty acid component may be saturated or may include one or more unsaturations. In some instances, the fatty acid component is fully saturated. In other instances, the fatty acid component is monounsaturated. In yet other instances, the fatty acid component is polyunsaturated, such as having 2, 3, 4 or more saturations. In some embodiments, the fatty acid is selected from palmitic acid, stearic acid, oleic acid, linoleic acid, myristoleic acid and batyl fatty acid.

Embodiments of the present disclosure describe an amorphous solid composition of a fatty acid metal salt. The term "amorphous" is used herein in its conventional sense to refer to a solid material that is characterized by undefined structural order and microscopic configurations that lack a regular geometric arrangement in three dimensions. In some embodiments, the amorphous solid composition of the fatty acid metal salt are not crystalline (i.e., a solid material where the molecules that form the solid are arranged in a highly ordered microscopic geometric configuration (e.g., form an ordered lattice-type structure) that extends in three dimensions)

In embodiments, the organic salt of the succinylated 3-(fatty acid amido)-2-hydroxy-1-(protected hydroxy)-propane may include, but is not limited to, a triethylamine salt, triethanolamine salt, an ammonium salt, an arginine salt, a benzathine salt, an ethylenediamine salt, a meglumine salt, a procaine salt, an N-methylglucamine salt, a piperazine salt, a tromethamine salt, an N,N'-dibenzylethylene-diamine salt, a chloroprocaine salt, a diethanolamine salt, an ethanolamine salt, a diisopropylamine salt, a diisopropylethylamine salt, among other organic cation salts. In certain embodiments, the succinylated 3-(fatty acid amido)-2-hydroxy-1-(protected hydroxy)-propane organic salt is a succinylated 3-(fatty acid amido)-2-hydroxy-1-(protected hydroxy)-propane triethylamine salt.

The succinylated 3-(fatty acid amido)-2-hydroxy-1-(protected hydroxy)-propane organic salt is contacted with a metal base in a solvent. Depending on the desired succinylated 3-(fatty acid amido)-2-hydroxy-1-(protected hydroxy)-propane metal salt, the metal base may include, but is not limited to lithium tert-butoxide, lithium hydroxide, lithium ethoxide, lithium isopropoxide, lithium methoxide, potassium tert-butoxide, potassium hydroxide, potassium ethoxide, potassium isopropoxide, potassium methoxide, sodium tert-butoxide, sodium hydroxide, sodium ethoxide, sodium isopropoxide, sodium methoxide, magnesium tert-butoxide, magnesium hydroxide, magnesium ethoxide, magnesium isopropoxide, magnesium methoxide, calcium tert-butoxide, calcium hydroxide, calcium ethoxide, calcium isopropoxide, calcium methoxide. In embodiments, the succinylated 3-(fatty acid amido)-2-hydroxy-1-(protected hydroxy)-propane organic salt is contacted in an amount sufficient to generate a succinylated 3-(fatty acid amido)-2-hydroxy-1-(protected hydroxy)-propane metal salt such as a succinylated 3-(fatty acid amido)-2-hydroxy-1-(protected hydroxy)-propane lithium salt, a succinylated 3-(fatty acid amido)-2-hydroxy-1-(protected hydroxy)-propane sodium salt, a succinylated 3-(fatty acid amido)-2-hydroxy-1-(protected hydroxy)-propane potassium salt, a succinylated 3-(fatty acid amido)-2-hydroxy-1-(protected hydroxy)-propane magnesium salt or a succinylated 3-(fatty acid amido)-2-hydroxy-1-(protected hydroxy)-propane calcium salt.

The amount of metal base contacted with the succinylated 3-(fatty acid amido)-2-hydroxy-1-(protected hydroxy)-propane organic salt may vary, ranging from 0.5 equivalents to 2 equivalents of metal base to succinylated 3-(fatty acid amido)-2-hydroxy-1-(protected hydroxy)-propane organic salt, such as from 0.75 equivalents to 1.85 equivalents, such as 1 equivalent to 1.8 equivalents, such as from 1.05 equivalents to 1.75 equivalents, such as from 1.10 equivalents to 1.70 equivalents, such as from 1.15 equivalents to 1.65 equivalents, such as from 1.2 equivalents to 1.6 equivalents, such as from 1.25 equivalents to 1.55 equivalents and including from 1.3 equivalents to 1.5 equivalents and including contacting the succinylated 3-(fatty acid amido)-2-hydroxy-1-(protected hydroxy)-propane organic salt with 1.5 equivalents of metal base.

In embodiments, the succinylated 3-(fatty acid amido)-2-hydroxy-1-(protected hydroxy)-propane organic salt is contacted with the metal base in a solvent. The solvent for contacting the succinylated 3-(fatty acid amido)-2-hydroxy-1-(protected hydroxy)-propane organic salt with the metal base may be any suitable solvent where the succinylated 3-(fatty acid amido)-2-hydroxy-1-(protected hydroxy)-propane organic salt and metal base are sufficiently soluble and may be polar or nonpolar. In some embodiments, the solvent is non-polar, such as pentane, hexane, heptane, octane or benzene. In other embodiments, the solvent is a polar solvent, such as dichloromethane, tetrahydrofuran, methyltetrahydrofuran, isopropylacetate, dimethylformamide, acetonitrile, toluene, 2-methylbutan-2-ol (tAmOH) and N-methyl-2-pyrrolidone. In certain embodiments, the succinylated 3-(fatty acid amido)-2-hydroxy-1-(protected hydroxy)-propane organic salt is contacted with the metal base in dichloromethane. In some embodiments, the succinylated 3-(fatty acid amido)-2-hydroxy-1-(protected hydroxy)-propane organic salt is contacted with the metal base by contacting the succinylated 3-(fatty acid amido)-2-hydroxy-1-(protected hydroxy)-propane organic salt with a solvent containing the metal base. In these embodiments, the solvent containing the metal base may be a non-polar solvent, such as pentane, hexane, heptane, octane or benzene. In certain embodiments, the solvent is hexane.

The succinylated 3-(fatty acid amido)-2-hydroxy-1-(protected hydroxy)-propane organic salt may be contacted with the metal base at a temperature that ranges from −10° C. to 10° C., such as from −9° C. to 9° C., such as from −8° C. to 8° C., such as from −7° C. to 7° C., such as from −6° C. to 6° C. and including from −5° C. to 5° C.

In some embodiments, the succinylated 3-(fatty acid amido)-2-hydroxy-1-(protected hydroxy)-propane organic salt may be contacted with the metal base at a first temperature and the reaction mixture is warmed to a second temperature. In one example, the succinylated 3-(fatty acid amido)-2-hydroxy-1-(protected hydroxy)-propane organic salt is contacted with the metal base in the solvent at a first temperature and then warmed to a second temperature. In another example, the succinylated 3-(fatty acid amido)-2-hydroxy-1-(protected hydroxy)-propane organic salt is contacted with the metal base in the solvent at a first temperature for a first period of time and then warmed to a second temperature for a second period of time. In these embodiments, the first temperature may vary, ranging from −10° C. to 0° C., such as from −9° C. to −1° C., such as from −8° C. to −2° C., such as from −7° C. to −3° C. and including from −6° C. to −4° C. The second temperature may also range, such as from 0° C. to 20° C., such as from 1° C. to 19° C., such as from 2° C. to 18° C., such as from 3° C. to 17° C., such as from 4° C. to 16° C., such as from 5° C. to 15° C. and including from 5° C. to 10° C. The duration of the first period of time may vary depending on the concentration of the metal salt and temperature and may range from 0.1 minutes to 30 minutes, such as from 0.5 minutes to 25 minutes, such as from 1 minute to 20 minutes, such as from 5 minutes to 15 minutes and including from 5 minutes to 10 minutes. In some embodiments, the metal base is contacted with the succinylated 3-(fatty acid amido)-2-hydroxy-1-(protected hydroxy)-propane organic salt and maintained in contact (e.g., stirring the reaction mixture) for the entire duration of the first period of time. In other embodiments, the metal base is dropwise added (or titrated) over all or part of the first period of time to the succinylated 3-(fatty acid amido)-2-hydroxy-1-(protected hydroxy)-propane organic salt in the solvent. The duration of the second period of time may vary, ranging from 0.1 minutes to 30 minutes, such as from 0.5 minutes to 25 minutes, such as from 1 minute to 20 minutes, such as from 5 minutes to 15 minutes and including from 5 minutes to 10 minutes.

In some embodiments, methods include precipitating the succinylated 3-(fatty acid amido)-2-hydroxy-1-(protected hydroxy)-propane metal salt from the reaction mixture to form an amorphous solid. To precipitate the amorphous solid succinylated 3-(fatty acid amido)-2-hydroxy-1-(protected hydroxy)-propane metal salt, the reaction mixture is contacted with the same or another nonpolar solvent to generate an amorphous solid succinylated 3-(fatty acid amido)-2-hydroxy-1-(protected hydroxy)-propane metal salt composition. The nonpolar solvent may include, but is not limited to pentane, hexanes, heptane, octane, benzene, among other nonpolar solvents. In certain embodiments, the succinylated 3-(fatty acid amido)-2-hydroxy-1-(protected hydroxy)-propane metal salt reaction mixture is contacted with heptane.

In some embodiments, methods include first cooling the succinylated 3-(fatty acid amido)-2-hydroxy-1-(protected hydroxy)-propane metal salt reaction mixture before contacting the reaction mixture with the non-polar solvent (e.g., heptane). For example, the reaction mixture may be cooled to a temperature that ranges from −10° C. to 10° C., such as from −9° C. to 9° C., such as from −8° C. to 8° C., such as from −7° C. to 7° C., such as from −6° C. to 6° C. and including from −5° C. to 5° C.

In precipitating the amorphous solid succinylated 3-(fatty acid amido)-2-hydroxy-1-(protected hydroxy)-propane metal salt, methods according to certain embodiments include concentrating the succinylated 3-(fatty acid amido)-2-hydroxy-1-(protected hydroxy)-propane metal salt in the non polar solvent (e.g., heptane), such as by heating or rotoevaporation. The volume of solvent in the the succinylated 3-(fatty acid amido)-2-hydroxy-1-(protected hydroxy)-propane reaction mixture may be reduced by 5% or more, such as by 10% or more, such as by 15% or more, such as by 20% or more, such as by 25% or more, such as by 30% or more, such as by 35% or more, such as by 40% or more, such as by 45% or more, such as by 50% or more, such as by 55% or more, such as by 60% or more, such as by 65% or more, such as 70% or more and including by 75% or more. This may be repeated one or more times, where an amount of the non-polar solvent is added to the succinylated 3-(fatty acid amido)-2-hydroxy-1-(protected hydroxy)-propane metal salt composition and then further concentrated, such as repeated two or more times, such as three or more times and including five or more times.

To precipitate the amorphous succinylated 3-(fatty acid amido)-2-hydroxy-1-(protected hydroxy)-propane metal salt from the non-polar solvent, the composition in the non-polar solvent (e.g., heptane) may be first heated to produce a heated succinylated 3-(fatty acid amido)-2-hydroxy-1-(protected hydroxy)-propane metal salt composition and then cooled to form the amorphous solid succinylated 3-(fatty acid amido)-2-hydroxy-1-(protected hydroxy)-propane metal salt. The succinylated 3-(fatty acid amido)-2-hydroxy-1-(protected hydroxy)-propane metal salt may be heated in the nonpolar solvent to a temperature that ranges from 20° C. to 60° C., such as from 25° C. to 60° C., such as from 40° C. to 55° C. and including from 45° C. to 55° C. The heated composition may be maintained at the elevated temperature for a duration that varies, such as for 1 minute or longer, such as for 2 minutes or longer, such as for 5 minutes or longer, such as 10 minutes or longer, such as 15 minutes or longer, such as 30 minutes or longer and including for 60 minutes or longer. In certain embodiments, methods include heating the composition until the succinylated 3-(fatty acid amido)-2-hydroxy-1-(protected hydroxy)-propane metal salt is solubilized into the solvent, such as by observing a clear solution by visual inspection.

The heated composition is cooled to precipitate the succinylated 3-(fatty acid amido)-2-hydroxy-1-(protected hydroxy)-propane metal salt. The heated composition is cooled to a temperature of −20° C. to 20° C., such as from −19° C. to 19° C., such as from −18° C. to 18° C., such as from −17° C. to 17° C., such as from −16° C. to 16° C., such as from −15° C. to 15° C., such as from −14° C. to 14° C., such as from −13° C. to 13° C. such as from −12° C. to 12° C. such as from −11° C. to 11° C., such as from −10° C. to 10° C., and including from −5° C. to 5° C. In certain embodiments, the heated succinylated 3-(fatty acid amido)-2-hydroxy-1-(protected hydroxy)-propane metal salt composition is cooled to 0° C. The cooled composition may be maintained at the reduced temperature (e.g., at 0° C.) for a duration that varies, such as for 1 minute or longer, such as for 2 minutes or longer, such as for 5 minutes or longer, such as 10 minutes or longer, such as 15 minutes or longer, such as 30 minutes or longer and including for 60 minutes or longer. In certain embodiments, the cooled succinylated 3-(fatty acid amido)-2-hydroxy-1-(protected hydroxy)-propane metal salt composition is maintained at the reduced temperature (e.g., at 0° C.) for 60 minutes.

The amorphous solid succinylated 3-(fatty acid amido)-2-hydroxy-1-(protected hydroxy)-propane metal salt composition may be isolated by filtration (e.g., vacuum filtration) or the solvent may be removed by heating or rotoevaporation. In certain embodiments, the amorphous solid succinylated 3-(fatty acid amido)-2-hydroxy-1-(protected hydroxy)-propane metal salt composition is isolated by drying at room temperature under nitrogen atmosphere or under vacuum. In some embodiments, the amorphous solid succinylated 3-(fatty acid amido)-2-hydroxy-1-(protected hydroxy)-propane metal salt is isolated at a temperature of −20° C. to 20° C., such as from −19° C. to 19° C., such as from −18° C. to 18° C., such as from −17° C. to 17° C., such as from −16° C. to 16° C., such as from −15° C. to 15° C., such as from −14° C. to 14° C., such as from −13° C. to 13° C. such as from −12° C. to 12° C. such as from −11° C. to 11° C., such as from −10° C. to 10° C. and including from −5° C. to 5° C. In certain embodiments, the amorphous solid succinylated 3-(fatty acid amido)-2-hydroxy-1-(protected hydroxy)-propane metal salt is isolated at 0° C.

In some embodiments, methods include precipitating the amorphous solid succinylated 3-(fatty acid amido)-2-hydroxy-1-(protected hydroxy)-propane metal salt by an inverse addition of a non-polar solvent to the succinylated 3-(fatty acid amido)-2-hydroxy-1-(protected hydroxy)-propane metal salt reaction mixture. In this embodiment, an amount of the succinylated 3-(fatty acid amido)-2-hydroxy-1-(protected hydroxy)-propane metal salt reaction mixture is contacted with a non-polar solvent. The non-polar solvent may include, but is not limited to pentane, hexanes, heptane, octane, benzene, among other nonpolar solvents. In certain instances, the succinylated 3-(fatty acid amido)-2-hydroxy-1-(protected hydroxy)-propane metal salt reaction mixture is contacted with heptane.

The reaction mixture contacted with the non-polar solvent is concentrated, such as by heating or rotoevaporation. The volume of the reaction mixture may be reduced by 5% or more, such as by 10% or more, such as by 15% or more, such as by 20% or more, such as by 25% or more, such as by 30% or more, such as by 35% or more, such as by 40% or more, such as by 45% or more, such as by 50% or more, such as by 55% or more, such as by 60% or more, such as by 65% or more, such as 70% or more and including by 75% or more. This may be repeated one or more times, where an amount of the non-polar solvent is added to the succinylated 3-(fatty acid amido)-2-hydroxy-1-(protected hydroxy)-propane metal salt composition and then further concentrated, such as repeated two or more times, such as three or more times and including five or more times.

To precipitate the amorphous succinylated 3-(fatty acid amido)-2-hydroxy-1-(protected hydroxy)-propane metal salt from the non-polar solvent, the composition is heated to produce a heated succinylated 3-(fatty acid amido)-2-hydroxy-1-(protected hydroxy)-propane metal salt composition. The composition may be heated in the nonpolar solvent to a temperature that ranges from 20° C. to 60° C., such as from 25° C. to 60° C., such as from 40° C. to 55° C. and including from 45° C. to 55° C. The heated composition may be maintained at the elevated temperature for a duration that varies, such as for 1 minute or longer, such as for 2 minutes or longer, such as for 5 minutes or longer, such as 10 minutes or longer, such as 15 minutes or longer, such as 30 minutes or longer and including for 60 minutes or longer. In certain embodiments, methods include heating the composition until the succinylated 3-(fatty acid amido)-2-hydroxy-1-(protected hydroxy)-propane metal salt is solubilized into the solvent, such as by observing a clear solution by visual inspection.

To cool the heated succinylated 3-(fatty acid amido)-2-hydroxy-1-(protected hydroxy)-propane metal salt composition, the heated composition is contacted with a cold non-polar solvent (e.g., heptane) In these embodiments, the heated succinylated 3-(fatty acid amido)-2-hydroxy-1-(protected hydroxy)-propane metal salt composition may be added to a non-polar solvent (e.g., heptane) that is at a temperature of −20° C. to 20° C., such as from −19° C. to 19° C., such as from −18° C. to 18° C., such as from −17° C. to 17° C., such as from −16° C. to 16° C., such as from −15° C. to 15° C., such as from −14° C. to 14° C., such as from −13° C. to 13° C. such as from −12° C. to 12° C. such as from −11° C. to 11° C., such as from −10° C. to 10° C. and including from −5° C. to 5° C. In certain embodiments, the heated succinylated 3-(fatty acid amido)-2-hydroxy-1-(protected hydroxy)-propane metal salt composition is contacted with a non-polar solvent that is at a temperature of −10° C. The cooled composition may be maintained at the reduced temperature (e.g., at 0° C.) for a duration that varies, such as for 0.1 hours or longer, such as for 0.5 hours or longer, such as for 1 hour or longer, such as for 1.5 hours or longer, such as for 2 hours or longer, such as for 2.5 hours or longer and including for 3 hours or longer. In certain embodiments, the cooled succinylated 3-(fatty acid amido)-2-hydroxy-1-(protected hydroxy)-propane metal salt composition is maintained at the reduced temperature (e.g., at 0° C.) for 3 hours.

In certain embodiments, methods include conducting one or more heating/cooling cycles on the succinylated 3-(fatty acid amido)-2-hydroxy-1-(protected hydroxy)-propane metal salt composition. In these embodiments, each heating/cooling cycle includes heating the succinylated 3-(fatty acid amido)-2-hydroxy-1-(protected hydroxy)-propane metal salt composition to a first temperature and maintaining the composition at the first temperature for a first period of time, followed by cooling the heated composition to a second temperature and maintaining the cooled compositioned at the second temperature for a second period of time. In these embodiments, the first temperature ranges from 10° C. to 30° C., such as from 15° C. to 25° C. and including to a temperature of 20° C. and the first period of time ranges from 30 minutes to 60 minutes, such as from 35 minutes to 55 minutes and including from 40 minutes to 50 minutes. The second temperature ranges from −10° C. to 10° C., such as from −5° C. to 5° C. and including 0° C. and the second period of time ranges from 45 minutes to 90 minutes, such as from 50 minutes to 85 minutes, such as from 55 minutes to 80 minutes and including from 60 minutes to 75 minutes. The heating/cooling cycle may be repeated one or more times, such as two or more times and including three or more times.

The precipitated succinylated 3-(fatty acid amido)-2-hydroxy-1-(protected hydroxy)-propane metal salt composition in the non-polar solvent may be maintained at a reduced temperature for a period of time before isolation. In some instances, the precipitated succinylated 3-(fatty acid amido)-2-hydroxy-1-(protected hydroxy)-propane metal salt composition is maintained in the non-polar solvent at a temperature ranges from −10° C. to 10° C., such as from −5° C. to 5° C. and including 0° C. The precipitated succinylated 3-(fatty acid amido)-2-hydroxy-1-(protected hydroxy)-propane metal salt composition may be maintained at the reduced temperature for a period of time that varies, such as for 1 hour or longer, such as for 2 hours or longer, such as for 4 hours or longer, such as for 8 hours or longer, such as from 12 hours or longer and including for 16 hours or longer.

The amorphous solid succinylated 3-(fatty acid amido)-2-hydroxy-1-(protected hydroxy)-propane metal salt composition may be isolated by filtration (e.g., vacuum filtration) or the solvent may be removed by heating or rotoevaporation. In certain embodiments, the amorphous solid succinylated 3-(fatty acid amido)-2-hydroxy-1-(protected hydroxy)-propane metal salt composition is isolated by drying at room temperature under nitrogen atmosphere or under vacuum. In some embodiments, the amorphous solid succinylated 3-(fatty acid amido)-2-hydroxy-1-(protected hydroxy)-propane metal salt is isolated at a temperature of −20° C. to 20° C., such as from −19° C. to 19° C., such as from −18° C. to 18° C., such as from −17° C. to 17° C., such as from −16° C. to 16° C., such as from −15° C. to 15° C., such as from −14° C. to 14° C., such as from −13° C. to 13° C. such as from −12° C. to 12° C. such as from −11° C. to 11° C., such as from −10° C. to 10° C. and including from −5° C. to 5° C. In certain embodiments, the amorphous solid succinylated 3-(fatty acid amido)-2-hydroxy-1-(protected hydroxy)-propane metal salt is isolated at 0° C. The isolated amorphous solid succinylated 3-(fatty acid amido)-2-hydroxy-1-(protected hydroxy)-propane metal salt may be dried to remove any residual solvent, such as under vacuum at ambient temperature.

In certain embodiments, methods further include preparing the succinylated 3-(fatty acid amido)-2-hydroxy-1-(protected hydroxy)-propane organic salt by contacting a 3-(fatty acid amido)-2-hydroxy-1-(protected hydroxy)-propane with succinic anhydride in the presence of an organic base. The amount of succinic anhydride contacted with the 3-(fatty acid amido)-2-hydroxy-1-(protected hydroxy)-propane may vary, ranging from 0.5 equivalents to 2 equivalents of succinic anhydride to 3-(fatty acid amido)-2-hydroxy-1-(protected hydroxy)-propane, such as from 0.75 equivalents to 1.95 equivalents, such as 1 equivalent to 1.9 equivalents, such as from 1.1 equivalents to 1.85 equivalents, such as from 1.15 equivalents to 1.80 equivalents, such as from 1.25 equivalents to 1.75 equivalents and including contacting the 3-(fatty acid amido)-2-hydroxy-1-(protected hydroxy)-propane with 1.2 equivalents of succinic anhydride.

Depending on the type of organic salt desired, the organic base used may include, but is not limited to, triethylamine, triethanolamine, ammonia, arginine, benzathine, ethylenediamine, meglumine, procaine, N-methylglucamine, piperazine, tromethamine, N,N'-dibenzylethylene-diamine, chloroprocaine, diethanolamine, ethanolamine, diisopropylamine, diisopropylethylamine, among other organic bases. In these embodiments, the 3-(fatty acid amido)-2-hydroxy-1-(protected hydroxy)-propane is contacted with succinic anhydride in a polar solvent, such as dichloromethane, tetrahydrofuran, methyltetrahydrofuran, isopropylacetate, dimethylformamide, acetonitrile, toluene, 2-methylbutan-2-ol (tAmOH) and N-methyl-2-pyrrolidone. The amount of organic base used may vary, ranging from 2.5 equivalents to 3.5 equivalents of organic base to 3-(fatty acid amido)-2-hydroxy-1-(protected hydroxy)-propane, such as from 2.6 equivalents to 3.4 equivalents, such as 2.7 equivalent to 3.3 equivalents, such as from 2.8 equivalents to 3.2 equivalents, such as from 2.9 equivalents to 3.1 equivalents and including contacting the 3-(fatty acid amido)-2-hydroxy-1-(protected hydroxy)-propane with 3.0 equivalents of organic base (e.g., trimethylamine).

The 3-(fatty acid amido)-2-hydroxy-1-(protected hydroxy)-propane may be contacted with succinic anhydride in the presence of the organic base at a temperature that ranges from 10° C. to 30° C., such as from 12° C. to 28° C., such as from 14° C. to 26° C., such as from 16° C. to 24° C. and including from 18° C. to 22° C.

The components used in each step of the subject methods for preparing the amorphous succinylated 3-(fatty acid amido)-2-hydroxy-1-(protected hydroxy)-propane metal salt described herein may be a purified composition or a crude composition as desired. The term "purified" is used in its conventional sense to refer to a composition where at least some isolation or purification process has been conducted, such as for example, filtration or aqueous workup of a reaction mixture. In certain instances, purification includes liquid chromatography, recrystallization, distillation (e.g., azeotropic distillation) or other type of compound purification. In some embodiments, a reaction mixture is used in a subsequent step in the methods described herein as a crude mixture. The term "crude" is used herein in its conventional sense to refer to a composition where no purification or other workup of the reaction mixture has been conducted. In certain instances, the crude composition reaction mixtures include the compound of interest in sufficient purity such as where the crude composition includes a compound of interest in a purity of 90% or greater, 91% or greater, 92% or greater, 93% or greater, 94% or greater, such as 95% or greater, 96% or greater, such as 97% or greater, 98% or greater, and including 99% or greater, as determined by high performance liquid chromatography (HPLC), proton nuclear magnetic resonance spectroscopy ($^1$H NMR) or a combination thereof. For example, in certain embodiments as described above, methods include preparing the succinylated 3-(fatty acid amido)-2-hydroxy-1-(protected hydroxy)-propane organic salt by contacting a 3-(fatty acid amido)-2-hydroxy-1-(protected hydroxy)-propane with succinic anhydride in the presence of an organic base. In these embodiments, methods may include contacting the crude composition of succinylated 3-(fatty acid amido)-2-hydroxy-1-(protected hydroxy)-propane organic salt with the metal base directly (i.e., without any purification or workup) to produce the succinylated 3-(fatty acid amido)-2-hydroxy-1-(protected hydroxy)-propane metal salt.

In embodiments, the fatty acid of the 3-(fatty acid amido)-2-hydroxy-1-(protected hydroxy)-propane compounds (i.e., organic salt, metal salt, etc.) as described herein may vary, where in certain instances, the fatty acid is selected from palmitic acid, stearic acid, oleic acid, linoleic acid, myristoleic acid and batyl fatty acid.

The protected hydroxy group of the 3-(fatty acid amido)-2-hydroxy-1-(protected hydroxy)-propane compounds as described herein may also vary, where in certain instances, the hydroxyl protective group includes, but is not limited to: 1) an alkyl ether-type protective group, such as an alkyl ether, allyl ether, triphenylmethyl ether, dimethoxy-triphenylmethyl ether, benzyl ether or p-methoxybenzyl ether protecting group; 2) an ester and carbonate-type protective group, such as an acetate, chloroacetate, dichloroacetate, trichloroacetate, trifluoroacetate, pivaloate, benzoate, p-methoxybenzoate, p-bromobenzoate, methyl carbonate, 9-(fluorenylmethyl) carbonate (Fmoc), allyl carbonate (Alloc), 2,2,2-trichloroethyl carbonate (Troc), 2-(trimethylsilyl) ethyl carbonate (Teoc), benzyl carbonate (Cbz), t-butyl carbonate (Boc) or dimethylthiocarbmate (DMTC) protecting group; 3) an acetal type protective group, such as a methoxymethyl ether (MOM), benzyloxymethyl ether (BOM), 2,2,2-trichloroethoxymethyl ether, 2-methoxymethyl ether (MEM), methylthiomethyl ether (MTM), p-methoxybenzyloxymethyl ether (PMBM), 2-(trimethylsilyl)ethoxymethyl ether (SEM), tetrahydropyranyl ether (THP) protecting group; and 2) a silyl ether type protective group, such as a trimethylsilyl (TMS), triethylsilyl (TES), isopropyldimethylsilyl (IPDMS), diethylisopropylsilyl (DEIPS), t-butyldimethylsilyl (TBS), t-butyldiphenylsilyl (TBDPS), triisopropylsilyl (TIPS), tetraisopropyldisiloxanylidene (TIPDS) or di-t-butylsilylene (DTBS) protecting group. In certain embodiments, the protected hydroxy group of the 3-(fatty acid amido)-2-hydroxy-1-(protected hydroxy)-propane compounds described herein is a dimethoxy-triphenylmethyl protecting group.

In certain embodiments, the succinylated 3-(fatty acid amido)-2-hydroxy-1-(protected hydroxy)-propane metal salt is a compound of Formula I:

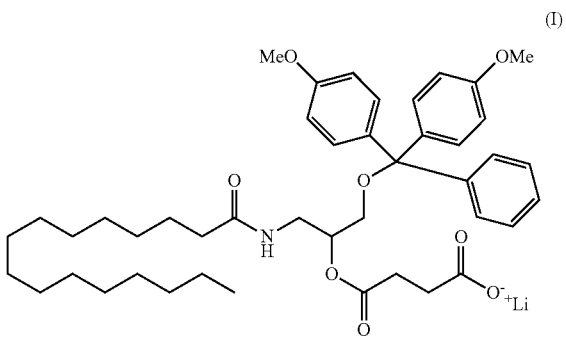 [SMILES: CCCCCCCCCCCCCCCC(=O)NCC(COC(c1ccccc1)(c1ccc(OC)cc1)c1ccc(OC)cc1)OC(=O)CCC(=O)[O-] ; [Li+]]

Figure 3:
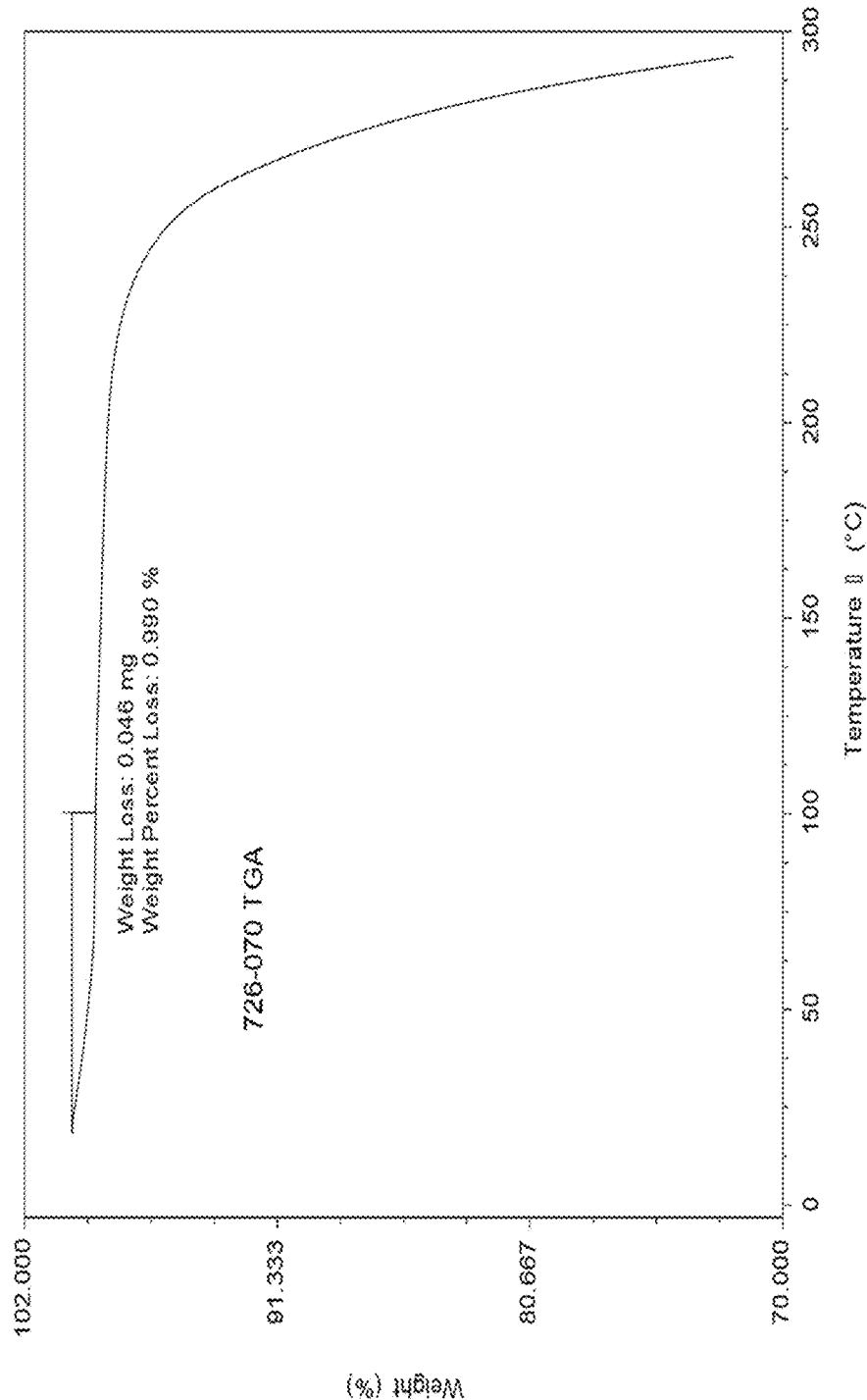
FIG. 3 shows a thermogram from thermogravimetric analysis (TGA) of an amorphous solid succinylated 3-(palmitoyl amido)-2-hydroxy-1-(dimethoxytriphenylmethyl hydroxy)-propane lithium salt according to certain embodiments.

In some embodiments, the present disclosure also provides an amorphous solid succinylated 3-(fatty acid amido)-2-hydroxy-1-(protected hydroxy)-propane lithium salt of Formula I having a peak at about 19.5° 2θ in an X-ray powder diffraction pattern (XRPD, FIG. 1) with Cu Kα radiation. In other embodiments, the present disclosure provides an amorphous solid succinylated 3-(fatty acid amido)-2-hydroxy-1-(protected hydroxy)-propane lithium salt of Formula I where thermogravimetric analysis (TGA, FIG. 3) exhibits a single weight loss step. In these embodiments, the single weight loss step may begin at about 225° C. The subject amorphous solid succinylated 3-(fatty acid amido)-2-hydroxy-1-(protected hydroxy)-propane lithium salt of Formula I may also be characterized by TGA thermogram that shows a mass loss of less than 1% of the total mass of the sample upon heating from 30° C. to 300° C. In other embodiments, the present disclosure provides an amorphous solid succinylated 3-(fatty acid amido)-2-hydroxy-1-(protected hydroxy)-propane lithium salt of Formula I, where the differential scanning calorimetry (DSC, FIG. 4) curve exhibits an absorption peak at about 44.9° C.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pl, picoliter(s); s or see, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4$^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. A variety of examples of synthetic routes that can be used to synthesize the compounds disclosed herein are described in the schemes below.

Example 1—Preparation of an Amorphous Solid Succinylated 3-(palmitoyl amido)-2-hydroxy-1-(dimethoxytriphenylmethyl hydroxy)-propane lithium salt from 3-(palmitoyl amido)-2-hydroxy-1-(dimethoxytriphenylmethyl protected hydroxy)-propane (Scheme II)

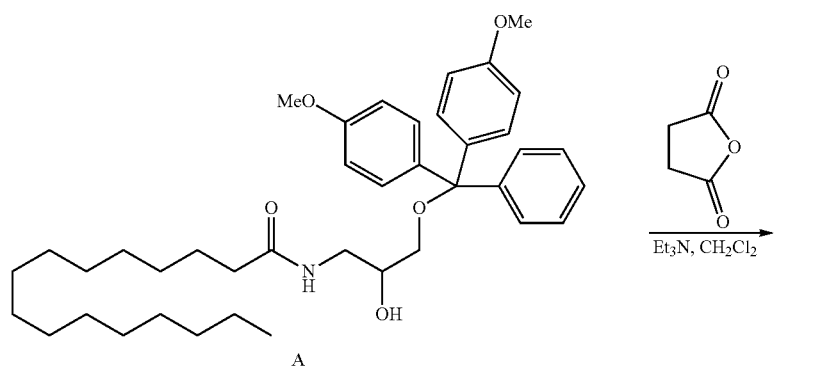

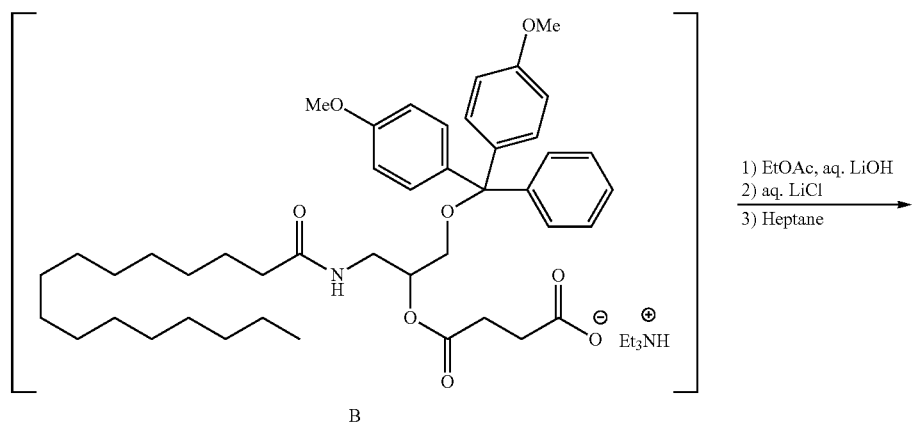

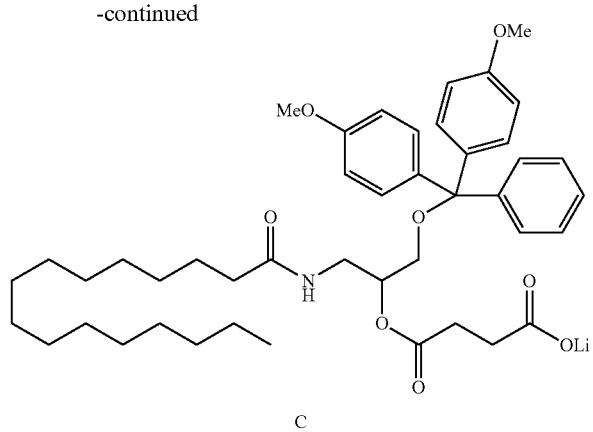

C 3-(palmitoyl amido)-2-hydroxy-1-(dimethoxytriphenylmethyl protected hydroxy)-propane (A) was contacted with succinic anhydride in the presence of triethylamine in dichloromethane. The solution was stirred at room temperature for 3 hours to form the succinylated 3-(palmitoyl amido)-2-hydroxy-1-(dimethoxytriphenylmethyl hydroxy)-propane triethylamine salt intermediate (B) without isolation. The succinylated 3-(palmitoyl amido)-2-hydroxy-1-(dimethoxytriphenylmethyl hydroxy)-propane triethylamine salt intermediate was diluted with ethyl acetate and cooled to 0-5° C. followed by addition of aqueous LiOH and stirred at 0-5° C. for 5-10 minutes. The aqueous layer and organic layer containing the lithium salt were separated and the organic layer was washed with LiCl. The organic layer was again separated and concentrated by rotoevaporation. The concentrate was diluted with ethyl acetate and poured through a sintered glass funnel. The clear filtrate was concentrated by rotoevaporation and dried by vacuum pump until a foamed solid was formed. Heptane was added to the foamed solid and heated to 50° C. until clear. The clear solution was cooled to 45° C. over 1 hour until hazy. Further cooling to 20° C. over 1 hour resulted in the formation of a gummy solid. The composition was further cooled to 5-10° C. until the composition formed hard solids. The slurry containing the hard solids was stirred at 10° C. overnight. The hard solids were isolated by filtration and was dried under vacuum with a nitrogen blanket at room temperature for 30 minutes. The solid was further dried under vacuum at ambient temperature for 16 hours.

Example 2—Preparation of an Amorphous Solid Succinylated 3-(fatty acid amido)-2-hydroxy-1-(protected hydroxy)-propane lithium salt—Normal Addition Mode Succinylated 3-(palmitoyl amido)-2-hydroxy-1-(dimethoxytriphenylmethyl protected hydroxy)-propane triethylamine salt was converted to lithium salt via non-aqueous treatment of 1N LiOtBu in hexane. The crude succinylated 3-(palmitoyl amido)-2-hydroxy-1-(dimethoxytriphenylmethyl protected hydroxy)-propane organic salt composition was cooled to 0-5° C. followed by addition of 1N LiOtBu in hexane (1.15 equivalents) and stirred at 0-5° C. for 5-10 minutes. Heptane was added to the composition and concentrated by rotoevaparation down to 10-15 mL. The addition of heptane and concentration by rotoevaporation was repeated twice. The lithium salt composition in heptane was heated to 50° C. until clear. The heated composition was maintained at 50° C. for 10-15 minutes under agitation, followed by cooling to 0° C. over 1 hour until the formation of gummy semi-solid. The slurry was aged at 0° C. for 3 hours followed by filtration at 0° C. under nitrogen gas. The solids were further dried under nitrogen and partial vacuum at 0° C. for 30 minutes and then at 10° C. for 30 minutes. The solid succinylated 3-(palmitoyl amido)-2-hydroxy-1-(dimethoxytriphenylmethyl protected hydroxy)-propane lithium salt was dried under vacuum at room temperature for 16 hours.

Dry free-flowing solids were obtained in 91% isolated yield (uncorrected), with >99.0A % purity by HPLC, which were proved as the succinylated 3-(palmitoyl amido)-2-hydroxy-1-(dimethoxytriphenylmethyl protected hydroxy)-propane lithium salt by ¹H NMR (DMSO-d6).

Example 3—Preparation of an Amorphous Solid Succinylated 3-(palmitoyl amido)-2-hydroxy-1-(dimethoxytriphenylmethyl hydroxy)-propane lithium salt—Inverse Addition Mode To avoid the phase transition going through an oily/sticky phase, inverse addition of hot T375-Li/heptane solution into cold heptane was designed and tested. The experiment was conducted in 100 mL EasyMax vessel with intensive mixing. The hot (50° C.) heptane solution of succinylated 3-(palmitoyl amido)-2-hydroxy-1-(dimethoxytriphenylmethyl hydroxy)-propane lithium salt described in Example 1 was added slowly (portion-wise) to cold heptane (−10° C.). Succinylated 3-(palmitoyl amido)-2-hydroxy-1-(dimethoxytriphenylmethyl hydroxy)-propane lithium salt solids were precipitated out immediately as uniform fine solids. The slurry formed in the heptane was aged at 0° C. for 3 hours. A heating/cooling cycle was conducted where the cooled slurry was heated from 0° C. to 20° C. over 40 minutes and maintained at 20° C. for 10 minutes followed by cooling to 0° C. over 1 hour and maintained at 0° C. for 1 hour. The heating/cooling cycle was repeated twice, followed by aging of the slurry at 0° C. for 16 hours. While the slurry batch temperature was kept at 0-10° C. there were no oily or sticky materials observed during and after addition of the succinylated 3-(palmitoyl amido)-2-hydroxy-1-(dimethoxytriphenylmethyl hydroxy)-propane lithium salt solution.

The fast filtration rate of final succinylated 3-(palmitoyl amido)-2-hydroxy-1-(dimethoxytriphenylmethyl hydroxy)-propane lithium salt solids indicated particle size increase by heat-cool cycling. De-liquor was conducted with vacuum at ambient temperature under nitrogen protection. The wet cake was dried overnight in a flask under vacuum at ambient temperature. The isolated succinylated 3-(palmitoyl amido)-2-hydroxy-1-(dimethoxytriphenylmethyl hydroxy)-propane lithium salt product (4.92 g) gave 91% yield (uncorrected). Product loss in mother liquor was 4.6%, by HPLC analysis It should be noticed that there was no impurity rejection by mother liquor.

Figure 2:
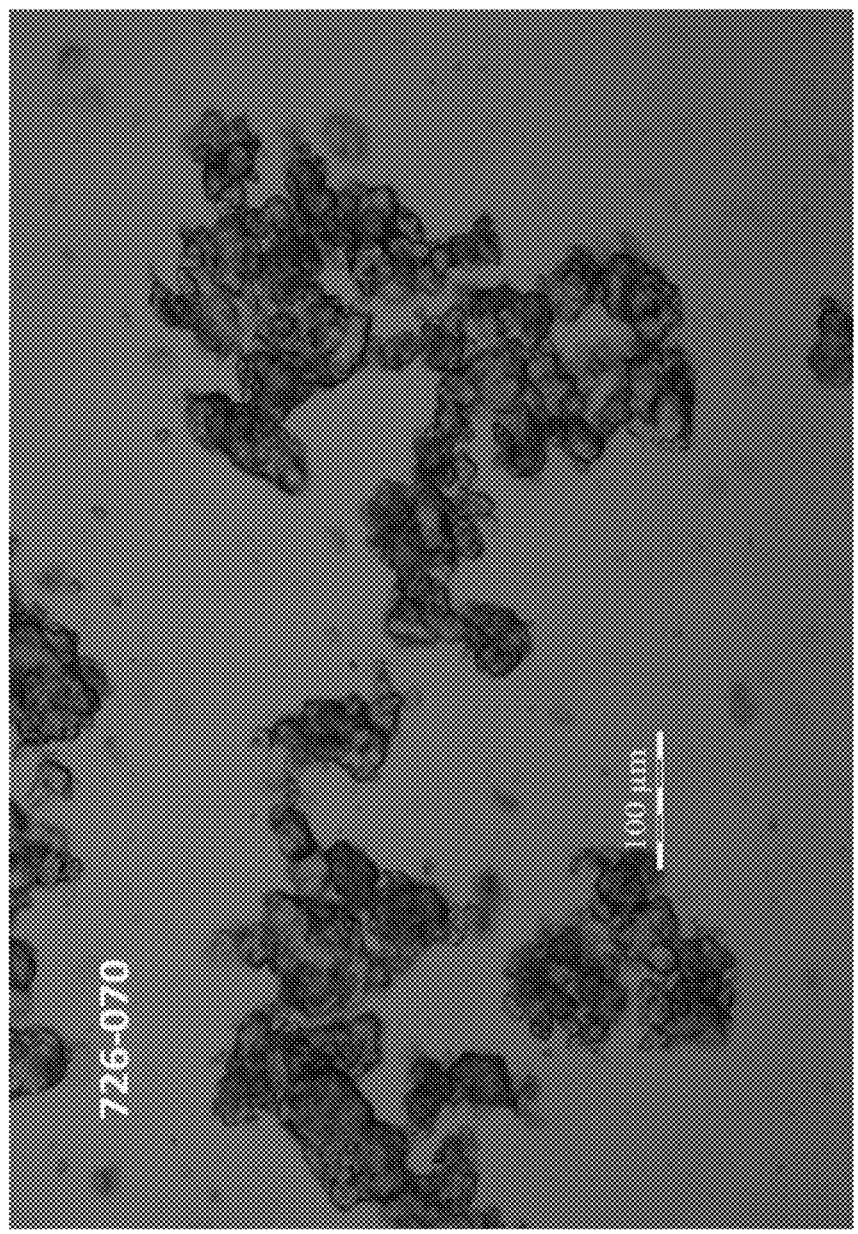
FIG. 2 shows a polarized microscopy image of an amorphous solid succinylated 3-(palmitoyl amido)-2-hydroxy-1-(dimethoxytriphenylmethyl hydroxy)-propane lithium salt according to certain embodiments.
Figure 4:
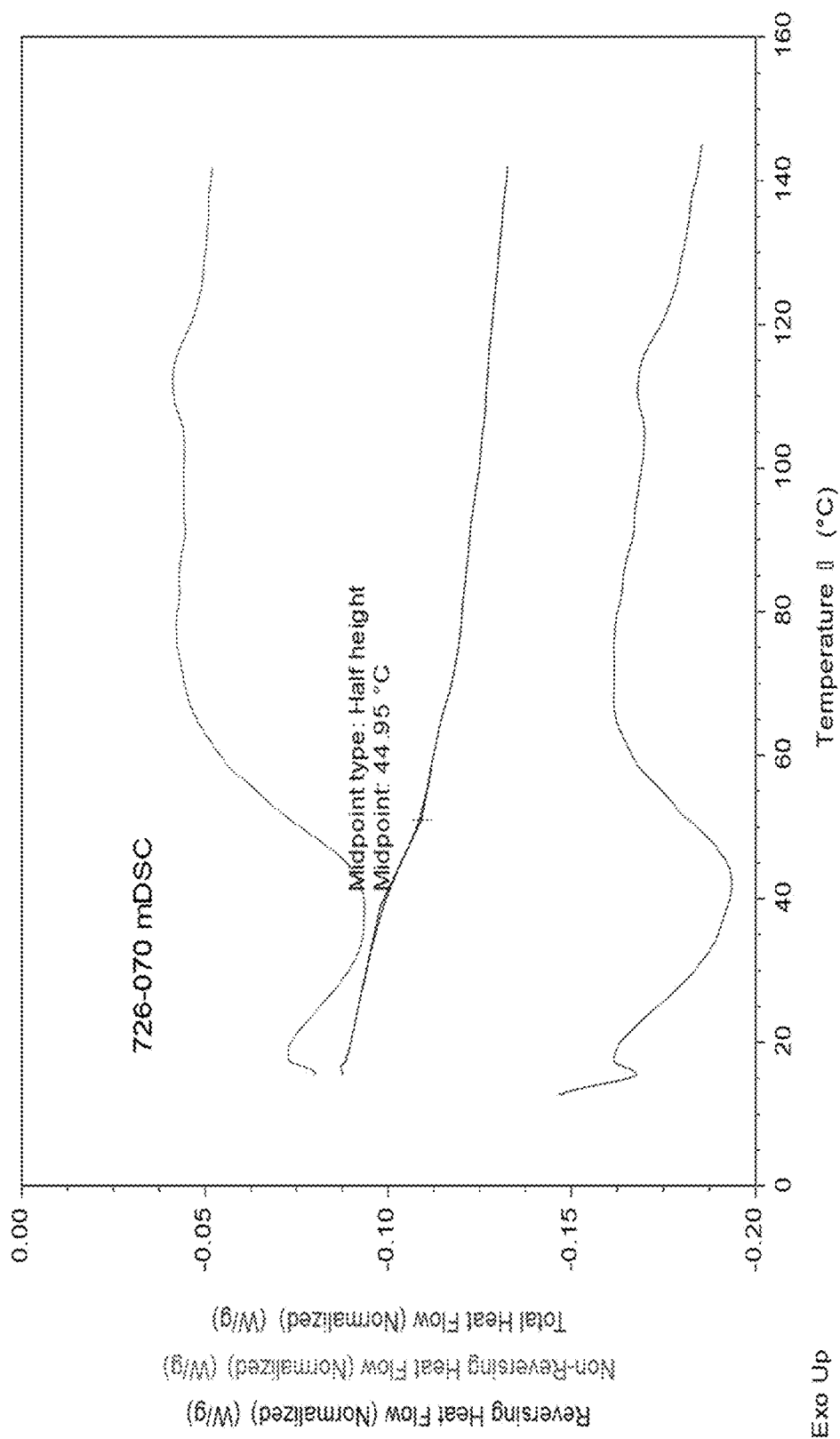
FIG. 4 shows a plot from differential scanning calorimetry of an amorphous solid succinylated 3-(palmitoyl amido)-2-hydroxy-1-(dimethoxytriphenylmethyl hydroxy)-propane lithium salt according to certain embodiments.

The isolated dry solids of the succinylated 3-(palmitoyl amido)-2-hydroxy-1-(dimethoxytriphenylmethyl hydroxy)-propane lithium salt from inverse addition protocol was characterized by X-ray powder diffraction (XRPD, FIG. 1), polarized light microscopy (PLM, FIG. 2), thermogravimetric analysis (TGA, FIG. 3), differential scanning calorimetry (DSC, FIG. 4). Lithium content of 1.36 wt % was found vs 0.94 wt % in theoretical by elemental analysis.

Example 4—Physical Stability of Amorphous Solid Succinylated 3-(palmitoyl amido)-2-hydroxy-1-(dimethoxytriphenylmethyl hydroxy)-propane lithium salt The physical stability of the amorphous 3-(palmitoyl amido)-2-hydroxy-1-(dimethoxytriphenylmethyl hydroxy)-propane lithium salts were tested at room temperature under different relative humidity (RH). 300 mg of amorphous 3-(palmitoyl amido)-2-hydroxy-1-(dimethoxytriphenylmethyl hydroxy)-propane lithium salt was placed in uncapped scintillation vials at 11% RH, 33% RH and 75% RH for 30 days. (Table 1)

TABLE 1

Physical stability of amorphous 3-(palmitoyl amido)-2-hydroxy-1-(dimethoxytriphenylmethyl hydroxy)-propane lithium salts at room temperature under different RH

| RH (20-25° C.) | Observation |
| --- | --- |
| 11% | Remains free-flowing solids up to 14 days* |
| 33% | |
| 75% | Turns to sticky after 30 min |

*The samples in vials were examined by gently shaking briefly once in every day

As shown in Table 1, the amorphous 3-(palmitoyl amido)-2-hydroxy-1-(dimethoxytriphenylmethyl hydroxy)-propane lithium salts remained solid for an extended period of time at room temperature up to 33% relative humidity. The lithium salts are stable solids that are readily isolated and stored as compared to 3-(palmitoyl amido)-2-hydroxy-1-(dimethoxytriphenylmethyl hydroxy)-propane organic salts which formed viscous, sticky liquids at room temperature. The lithium salts are also highly soluble in most organic solvents at or below ambient temperature. The high stability, ready storage and high solubility make the 3-(palmitoyl amido)-2-hydroxy-1-(dimethoxytriphenylmethyl hydroxy)-propane lithium salt a better starting material for use in the synthesis of compounds that include a fatty acid amide linker (e.g., imetelstat) as compared to 3-(palmitoyl amido)-2-hydroxy-1-(dimethoxytriphenylmethyl hydroxy)-propane organic salts.

What is claimed is:

1. A method of preparing an amorphous solid composition comprising a fatty acid metal salt, the method comprising:
   contacting a 3-(fatty acid amido)-2-hydroxy-1-(protected hydroxy)-propane with succinic anhydride in the presence of an organic base in a polar solvent to produce a succinylated 3-(fatty acid amido)-2-hydroxy-1-(protected hydroxy)-propane organic salt;
   contacting the succinylated 3-(fatty acid amido)-2-hydroxy-1-(protected hydroxy)-propane organic salt with a metal base to produce a succinylated 3-(fatty acid amido)-2-hydroxy-1-(protected hydroxy)-propane metal salt as shown in Scheme I; and
   precipitating the succinylated 3-(fatty acid amido)-2-hydroxy-1-(protected hydroxy)-propane metal salt to produce an amorphous solid succinylated 3-(fatty acid amido)-2-hydroxy-1-(protected hydroxy)-propane metal salt composition, Scheme I

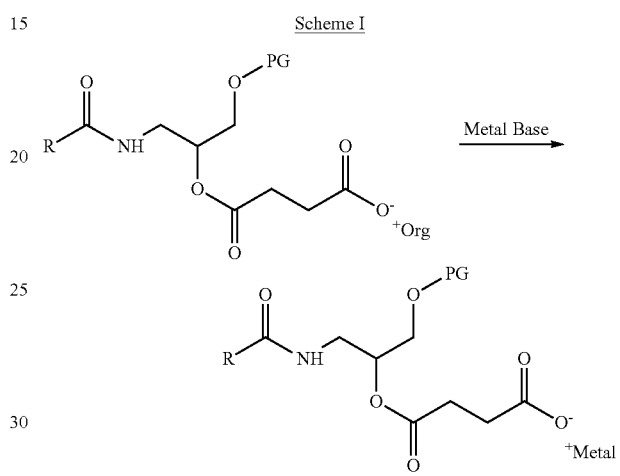

wherein R is a $C_{10}$-$C_{20}$ fatty acid, $^+$Org is an organic cation, and PG is a protecting group.

2. The method of claim 1, wherein the amorphous solid composition is a crude composition.

3. The method of claim 2, wherein the crude composition comprises the fatty acid metal salt having a purity of 90% or more as determined by high performance liquid chromatography (HPLC), proton nuclear magnetic resonance spectroscopy ($^1$H NMR) or a combination thereof.

4. The method of claim 1, wherein crude reaction products are carried through every step of the method.

5. The method of claim 4, wherein the method is sufficient to obtain the fatty acid metal salt in an isolated yield of 90% or more as determined by high performance liquid chromatography (HPLC), proton nuclear magnetic resonance spectroscopy ($^1$H NMR) or a combination thereof.

6. The method of claim 1, wherein the polar solvent comprises dichloromethane.

7. The method of claim 1, wherein precipitating the succinylated 3-(fatty acid amido)-2-hydroxy-1-(protected hydroxy)-propane metal salt comprises:
   heating the succinylated 3-(fatty acid amido)-2-hydroxy-1-(protected hydroxy)-propane metal salt in a non-polar solvent to produce a heated succinylated 3-(fatty acid amido)-2-hydroxy-1-(protected hydroxy)-propane metal salt composition; and
   cooling the heated succinylated 3-(fatty acid amido)-2-hydroxy-1-(protected hydroxy)-propane metal salt composition to form an amorphous solid of the succinylated 3-(fatty acid amido)-2-hydroxy-1-(protected hydroxy)-propane metal salt.

8. The method of claim 7, wherein cooling the heated succinylated 3-(fatty acid amido)-2-hydroxy-1-(protected hydroxy)-propane metal salt composition comprises inverse addition of the heated succinylated 3-(fatty acid amido)-2-hydroxy-1-(protected hydroxy)-propane metal salt composition to a cold non-polar solvent.

9. The method of claim 7, wherein the method comprises heating the succinylated 3-(fatty acid amido)-2-hydroxy-1-(protected hydroxy)-propane metal salt in the non-polar solvent to a temperature of 45-55° C.

10. The method of claim 7, wherein the method comprises cooling the heated succinylated 3-(fatty acid amido)-2-hydroxy-1-(protected hydroxy)-propane metal salt composition to a temperature of −10 to 0° C.

11. The method of claim 7, wherein the non-polar solvent comprises heptane.

12. The method of claim 7, wherein the amorphous solid of the succinylated 3-(fatty acid amido)-2-hydroxy-1-(protected hydroxy)-propane metal salt is isolated.

13. The method of claim 1, wherein the amorphous solid of the succinylated 3-(fatty acid amido)-2-hydroxy-1-(protected hydroxy)-propane metal salt is isolated by vacuum filtration.

14. The method of claim 1, wherein the fatty acid is selected from the group consisting of palmitic acid, stearic acid, oleic acid, linoleic acid, myristoleic acid and batyl fatty acid.

15. The method of claim 14, wherein the fatty acid is palmitic acid.

16. The method of claim 1, wherein the protected hydroxy group comprises a dimethoxy-triphenylmethyl protecting group.

17. The method of claim 1, wherein the 3-(fatty acid amido)-2-hydroxy-1-(protected hydroxy)-propane is a compound of Formula II:

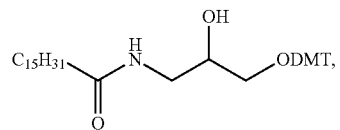

wherein DMT is dimethoxy-triphenylmethyl.

18. The method of claim 1, wherein the organic salt is a triethylamine salt.

19. The method of claim 1, wherein the metal base is selected from lithium hydroxide and lithium tert-butoxide.

20. The method of claim 19, wherein the metal base in lithium tert-butoxide.

21. The method of claim 1, wherein the succinylated 3-(fatty acid amido)-2-hydroxy-1-(protected hydroxy)-propane metal salt is a compound of Formula I:

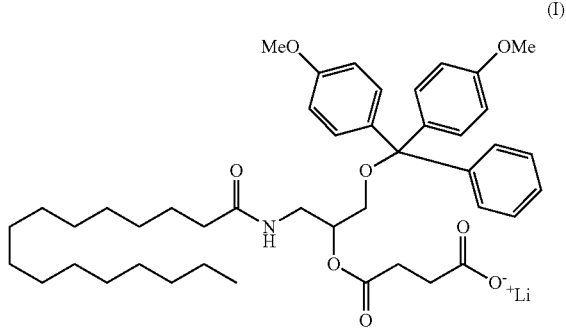 [SMILES: CCCCCCCCCCCCCCCC(=O)NCC(COC(c1ccccc1)(c1ccc(OC)cc1)c1ccc(OC)cc1)OC(=O)CCC(=O)[O-] ; [Li+]]

* * * * *

UNITED STATES PATENT AND TRADEMARK OFFICE
CERTIFICATE OF CORRECTION

PATENT NO. : 11,530,179 B2
APPLICATION NO. : 17/079129
DATED : December 20, 2022
INVENTOR(S) : Jennifer E. Albaneze-Walker It is certified that error appears in the above-identified patent and that said Letters Patent is hereby corrected as shown below:

In the Specification

In Column 24, Line 54, please change "see" to ---sec---.

Signed and Sealed this
Thirty-first Day of January, 2023

*Katherine Kelly Vidal*

Katherine Kelly Vidal
*Director of the United States Patent and Trademark Office*